United States Patent
Stobrawa et al.

(10) Patent No.: US 10,478,340 B2
(45) Date of Patent: *Nov. 19, 2019

(54) OPTICAL SYSTEM FOR A LASER THERAPY INSTRUMENT

(75) Inventors: Gregor Stobrawa, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 1311 days.

This patent is subject to a terminal disclaimer.

(21) Appl. No.: 14/116,471

(22) PCT Filed: Mar. 19, 2012

(86) PCT No.: PCT/EP2012/054743
§ 371 (c)(1),
(2), (4) Date: Jan. 2, 2014

(87) PCT Pub. No.: WO2012/156122
PCT Pub. Date: Nov. 22, 2012

(65) Prior Publication Data
US 2014/0114295 A1    Apr. 24, 2014

Related U.S. Application Data

(60) Provisional application No. 61/485,995, filed on May 13, 2011.

(30) Foreign Application Priority Data

May 13, 2011   (DE) .................. 10 2011 075 799

(51) Int. Cl.
*A61F 9/008*   (2006.01)
(52) U.S. Cl.
CPC .......... *A61F 9/008* (2013.01); *A61F 9/00825* (2013.01); *A61F 9/0084* (2013.01);
(Continued)

(58) Field of Classification Search
CPC ............ A61F 9/00825; A61F 9/0084; A61F 2009/0087; A61F 2009/00872; A61F 2009/00874; A61F 9/008–9/013
(Continued)

(56) References Cited

U.S. PATENT DOCUMENTS 5,837,962 A * 11/1998 Overbeck .............. B23K 26/06
                                                                219/121.6
6,741,359 B2 * 5/2004 Wei ........................ A61B 3/102
                                                                351/221
(Continued)

FOREIGN PATENT DOCUMENTS

DE    10 2005 013 949 A1    9/2006
DE    10 2008 027 358 A1    12/2009
(Continued)

OTHER PUBLICATIONS

European Search Report for Application No. 17167182.9, dated Nov. 23, 2017, 7 pages.

*Primary Examiner* — Gary Jackson
*Assistant Examiner* — Jonathan Kuo
(74) *Attorney, Agent, or Firm* — Patterson Thuente Pedersen, P.A.

(57) ABSTRACT

An optical system for a laser therapy instrument for the application of laser radiation on and in the eye, includes a femtosecond laser, an objective. The objective or at least one lens or lens group of the objective is shiftable in the direction of the optical axis being intended for shifting of the focus position from the region of the cornea to the region of the crystalline lens and vice versa. The optical system may include at least two optical assemblies designed for the axial variation of the focus of the therapeutic laser radiation, with the focus variation range Δz differing between the individual assemblies and a changing device, designed for the insertion of any one of these assemblies into the therapeutic laser beam path at a time.

15 Claims, 2 Drawing Sheets

(52) U.S. Cl.
CPC ............... *A61F 2009/0087* (2013.01); *A61F 2009/00872* (2013.01); *A61F 2009/00874* (2013.01)

(58) Field of Classification Search
USPC ........................................................ 606/4–6
See application file for complete search history.

(56) References Cited

U.S. PATENT DOCUMENTS

| | | | |
|---|---|---|---|
| 8,617,147 B2* | 12/2013 | Knox | A61F 9/008 606/5 |
| 9,554,943 B2* | 1/2017 | Sondermann | A61F 9/00825 |
| 2002/0060778 A1* | 5/2002 | Su | A61F 9/008 351/206 |
| 2008/0205249 A1* | 8/2008 | Bae | G11B 7/1275 369/112.23 |
| 2009/0131921 A1 | 5/2009 | Kurtz et al. | |
| 2009/0299347 A1* | 12/2009 | Vogler | A61F 9/008 606/5 |
| 2011/0028953 A1* | 2/2011 | Raksi | A61F 9/008 606/4 |
| 2011/0071509 A1* | 3/2011 | Knox | A61F 9/008 606/5 |

FOREIGN PATENT DOCUMENTS

| | | |
|---|---|---|
| DE | 10 2009 005 482 A1 | 7/2010 |
| DE | 11 2008 002 511 T5 | 7/2010 |
| DE | 11 2008 002 448 T5 | 11/2010 |
| GB | 2 359 375 A | 8/2001 |
| WO | WO 2012/130480 A1 | 10/2012 |

\* cited by examiner

OPTICAL SYSTEM FOR A LASER THERAPY INSTRUMENT

RELATED APPLICATIONS

The present application is a National Phase entry of PCT Application No. PCT/EP2012/054743, filed Mar. 19, 2012, which claims priority from DE Application No. 10 2011 075 799.6, filed May 13, 2011, and U.S. Patent Application No. 61/485,995, filed May 13, 2011, which applications are incorporated by reference herein in their entirety.

FIELD OF THE INVENTION

The present invention relates to an optical system for a laser therapy instrument for the application of laser radiation on and in the eye, suited particularly for laser surgery of the cornea and/or of the crystalline lens.

BACKGROUND

Laser therapy instruments are used, e.g., for correcting an ametropia of the human eye by a laser-surgical operation of the cornea. For this purpose, a lid is formed on the outer surface of the cornea, which lid is attached along one edge and is therefore known as a flap, and the thickness of which is substantially smaller then the thickness of the cornea. For correction, this flap is folded back, and from the surface of the region of the cornea that is now exposed, tissue is removed thereupon by application of a laser beam pulsed in the femtosecond range, in order to change the curvature of the cornea. Such an instrument is described in DE 10 2005 013 949 A1.

By contrast, a laser system described in DE 10 2008 027 358 A1 is intended for the analysis and treatment of the crystalline lens. Here, laser radiation also pulsed in the femtosecond range is focussed on to selected target spots in the region of the crystalline lens. At this wavelength, the detection of the laser light backscattered in the crystalline lens is possible at the greatest accuracy, and a refractive-surgical therapy of the crystalline lens can be performed with high precision.

Typically, in either case the interaction between the ultra-short laser pulses and the tissue takes place in a small volume, hereafter referred to as focus volume. Situated within the focus volume is the interaction zone, in which the structural change, section or removal of the tissue takes place. The laser focus must be precisely positioned at the locus of the desired interaction. This is done with an optical focusing system, which projects the parallel laser beam from infinity at the object side into the treatment plane on the image side.

This means that the precision achievable in the therapy is determined by the precision accuracy on the one hand, but also by the size of the interaction zone on the other. The size of the interaction zone, in turn, with a given laser pulse width, is essentially defined by the size of the focus volume. The smaller the focus volume, the smaller is the interaction zone, and the lesser is the risk of damage to the surrounding tissue, because with a small focus volume, the photon density needed for the treatment effect is achieved already with a very low laser pulse energy, such as about 10 nJ to 200 nJ; as a result, the energy input to the in the vicinity of the interaction zone is low.

The size of the focus volume varies with the parameters of the optical system and with the wavelength of the therapeutic laser radiation. In other words: in connection with a given wavelength, the desired small size of the focus volume is made possible by small aberrations and a fairly high numerical aperture. With increasing numerical aperture, not only the lateral dimension of the focus shrinks, but also its axial dimension. From the viewpoint of application, the numerical aperture should preferably be as high as possible.

The possibilities known in prior art of medical treatment of the cornea lying at the periphery of the eye on the one hand, and of the crystalline lens lying within the eye on the other, have the disadvantage that the instruments available satisfy the requirements of their respective special purpose only, which means that they differ, especially with regard to the focus position in the eye, the aperture and the size of the focus volume, to such an extent that they are designed and suitably either for therapy of the cornea alone or for therapy of the crystalline lens alone.

This requires extensive instrumentation that is ineffective both with regard to purchase costs and because several separate instruments are used below their capacity most of the time. In addition, setting up the several instruments separately for examining and treating the same patient eye is time-consuming.

While laser therapy instruments that can treat both the crystalline lens and the cornea are known, they are originally optimized only for the treatment of the crystalline lens. They can be used, e.g., to make access cuts for cataract operations, but the precision achievable with them is insufficient for creating a flap. This is because axial focus movements by several millimeters are required if the laser focus is to reach the entire anterior segment of the eye including the crystalline lens.

An essential problem to be solved in that respect is the fact that all object-side movements serving to vary the focus position (varying the parameters of the therapeutic laser beam before it enters the optical focussing system, e.g., by the shifting of lenses within the optical systems arranged further up the beam or by the movement of scanning mirrors) will inevitably result in a change of beam paths within the optical focussing system. The term "optical focussing system", in this context, stands for the objective from which the therapeutic laser radiation exits and is focussed on and directed at the eye. If, e.g., the axial position of the laser focus is shifted in this way, the aberrations occurring as a function of this variation will have a disadvantageous effect on the focus volume.

An optical focussing system or an objective that is optimized only for a particular focus position in axial direction always is a compromise between the spatial region accessible by the focus position and the size of the aberrations occurring within this region. As the same is true also for the lateral extension of the spatial region accessible by the laser focus, there is always a restriction of the entire spatial region in which the necessary focus quality is to be achieved.

SUMMARY OF THE INVENTION

Departing from this, the invention is based on the problem of creating an optical system for a laser therapy instrument which can be used alternately for laser surgery of the cornea and of the crystalline lens with high precision in both uses.

According to the invention, this problem is solved by an optical system having the features as described and claimed.

Note on the definition of terms: In the sense of the invention, the term "axial" defines the direction of the Z coordinate, and the term "lateral" defines the X and Y coordinate directions.

The inventive idea is based on the fact that the anterior segment of the eye consists essentially of two tissue regions that are of interest to laser surgery, i.e. the region of the cornea with a thickness of approximately 0.5 to 2 mm measured in the direction of radiation on the one hand, and the region of the crystalline lens with a substantially greater thickness of about 2 mm to 6 mm on the other hand. In between there is the anterior chamber filled with aqueous humour.

Consequently, for the most frequent therapies of the eye it is not necessary to design the optical system in such a way that the entire anterior segment of the eye can be accessed by the focus with an object-side axial scanning movement. It is sufficient to direct the focus separately to the region of the crystalline lens and the region of the cornea. Because of that, the actually very large object-side Z scanning range is limited to two separate tissue regions lying between the front surface of the cornea and the rear surface of the lens. While these tissue regions are spaced at a considerable distance from each other, one of them covers only slightly more than the cornea thickness and the other only slightly more than the thickness of the crystalline lens. This makes it possible to induce fewer aberrations.

According to an example embodiment of the invention, a configurable objective is used; in a first configuration, the focus position lies in a region comprising the cornea, and in a second configuration, the focus position lies in a region comprising the crystalline lens and the lens capsule. Both configurations can be achieved by at least one of the following measures:

Changes of air gaps between single or several lenses,
Changes of lens radii of one or several lenses,
Changes of refractive index of one or several lenses,
Insertion or exchange of single lenses or lens groups.

In that way, at least the two states are achieved that are optimally adapted to the respective focus position and thus have the least aberrations in these two configurations. This makes it possible to precisely vary the focus axially by object-side divergence variation in the region of the cornea or of the crystalline lens, respectively.

The optical assemblies arranged before the focussing objective in the direction of radiation for the purpose of divergence variation are so designed optically that the focus variation ranges $\Delta z$ for the cornea and also for the crystalline lens including the lens capsule are covered completely. According to the invention this is accomplished with certain "optical gear" ratios of the moved lenses or lens groups in these assemblies, in the context of the invention also called expanders. The gear ratio is designed to be a large as possible in order to achieve a very high accuracy of the Z position of the focus. According to the invention, the optical gear ratios between lens or lens group movements and focus position changes are computed or measured, saved as system parameters and taken into account by way of correction when the focus position is varied.

Axial resolution losses occurring upon switching between the two configurations are avoided in that the optical design of the expanders is coupled to the configuration change, for example, in that two expanders in the therapeutic laser beam path are exchanged against one another. Both expanders have beam path lengths which are independent of one another and are inserted into the beam path alternatingly depending on the configuration selected by the user.

Because of the varied depths of the focus positions in the anterior segment of the eye, there is, for each focus position, a maximum useful aperture, which is limited because of the free optical diameter of the optical focussing system and because of the anatomy of the eye, especially due to the shadowing of the iris in treatments of the crystalline lens. In case of smaller axial focus positions, such as occurring in treatments of the cornea, larger apertures can be used to advantage, with the associated advantages of the more compact focus volume, whereas in case of greater axial focus positions, i.e. in the region of the crystalline lens, it is of advantage not to fully utilize the technically available aperture of the optical focussing system but rather to use only the aperture that can effectively be utilized depending on the application. According to the invention, this is done by means of a reduced beam diameter at the entrance pupil of the optical focussing system.

The adaptation of the beam diameter to the configuration selected is accomplished by changing the expanders. In this way, a combined optical system results, which is adapted optimally to treatment of the cornea on the one hand, and, likewise optimally, to treatment of the crystalline lens on the other; this means that in either case the axial resolution is as high, and the numerical aperture as large, as possible technically and with regard to the application, while the aberrations of the system are, in either case, as small as possible.

It is also within the scope of embodiments of the invention to introduce a third axial focus variation range $\Delta z$ into optical system, e.g., for the purpose of manipulations in the anterior chamber of the eye, for vitreous body surgery or for therapies in the region of the retina.

The configuration change will also cause a change of field curvature depending on the real focus position. It is within the scope of the invention to compute or measure the field curvature, to save it as a system parameter as well and to take it into account in focussing by way of correction.

BRIEF DESCRIPTION OF THE DRAWINGS

Below, the invention will be explained in greater detail with reference to exemplary embodiments. In the accompanying drawings.

DETAILED DESCRIPTION

Figure 1:
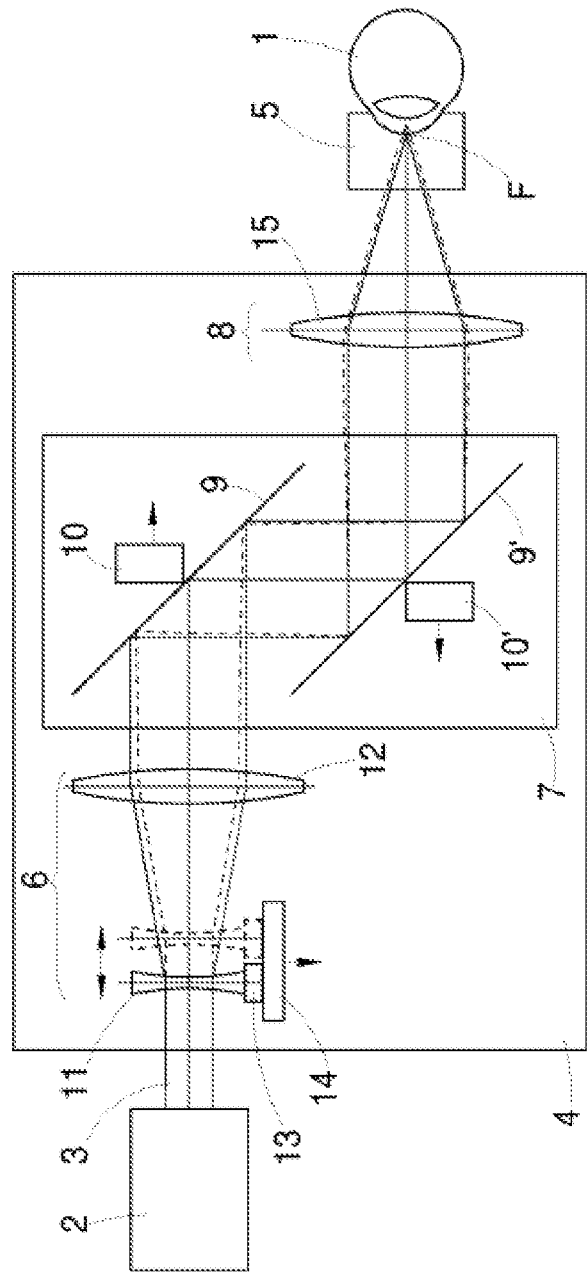
FIG. 1 is a schematic illustration of the optical system for a laser therapy instrument for the application of laser radiation as known in prior art.

The optical system shown in FIG. 1, for an instrument for therapy of a human eye 1 represents the present state of prior art. It comprises a radiation source 2, which delivers a beam 3 of pulsed laser radiation in the femtosecond range, and a scanning device 4, with which the beam 3 is focussed onto selected positions within the region of the cornea. On the cornea there is a contact glass 5 that has a concave contact surface and suppresses movements of the eye 1 during treatment.

The radiation source 2 is designed, e.g., to deliver laser radiation in the wavelength range around 1040 nm with a pulse width in the region of about 200 fs.

The scanning device 4 has, in the direction of the beam 3 originating from the radiation source 2, an optical assembly 6, behind which in the beam direction, there follows a deflecting device 7. According to given control signals, the deflecting device 7 deflects the beam 3 exiting the optical assembly 6 in a lateral direction, i.e. in X- and Y-direction across the Z-direction of the incident beam 3. In the beam path, the deflecting device 7 is followed by an objective 8, which focuses the beam 3 into the region of the cornea.

The deflecting device 7 is provided with two deflecting mirrors 9 and 9', which can be tilted about axes not shown in FIG. 1. In the simplified representation according to FIG. 1, the mirrors 9 and 9' are aligned in parallel, but actually the tilting axes are orthogonal to one another and to the optical axis of the optical assembly 6, so that tilting the first mirror 9 will deflect the beam 3 in Y-direction, and tilting the second mirror 9' will deflect it in X-direction orthogonal to it. The mirrors 9 and 9' are driven by actuators 10 and 10', respectively, which are connected with a control device via signal paths (marked by arrows). According to the desired focus position in lateral direction, the control device delivers control signals to the actuators 10 and 10', which thereupon cause the mirrors 9 and 9' to tilt. The deflecting mirrors 9 and 9' are spaced apart and a pupil optical system is located between deflecting mirrors 9 and 9'. The pupil optical system has, for example, an imaging ratio of 1:1.

The optical assembly 6 is provided with a lens 11 of negative refractive power that can be moved relative to the deflecting device 7, and a collecting lens 12. The lens 11 is connected with a straight-line guideway 13 along which it can be shifted with a variable optically effective distance from the deflecting device 7. The shifting of the lens 11 can be actuated, e.g., by a linear drive motor 14, which is also connected to the control device that is not shown. Depending on the desired focus position in Z-direction, the control device generates control signals that go to the linear drive motor 14.

Due to the design of the lens 11 and the collecting lens 12, the optical assembly 6 acts as an expander, which expands the diameter of the beam 3. If, then, a parallel beam 3 having a diameter d1 enters the optical assembly 6, the parallel beam 3 exiting the optical assembly 6 will have a diameter d2>d1.

The objective 8 is shows as a fixed lens 15; it focuses the beam 3 exiting the optical assembly 6 onto a position in the region of the cornea, this position being determined by means of the lens 11 and the deflecting device 7. The position of the focus F in the depth of the region of the cornea is determined by the shifting of the lens 11 along its optical axis. The lateral position of the focus F is determined by the deflecting device 7.

For further details of this, see publication DE 10 2005 013 949 A1.

Departing from the prior art as described above, the problem is solved by the invention in such a way that the objective 8 itself is shiftable along the optical axis or that an objective 8 is provided that consists of several lens groups, with at least one of these lens groups being shiftable along the optical axis. The shifting of the objective 8 or of the lens group of the objective 8 is relative to the eye and relative to the other assemblies of the system, in such a way that this change of distance causes a shift of the focus position from the region of the cornea to the region of the crystalline lens, and vice versa.

Figure 2:
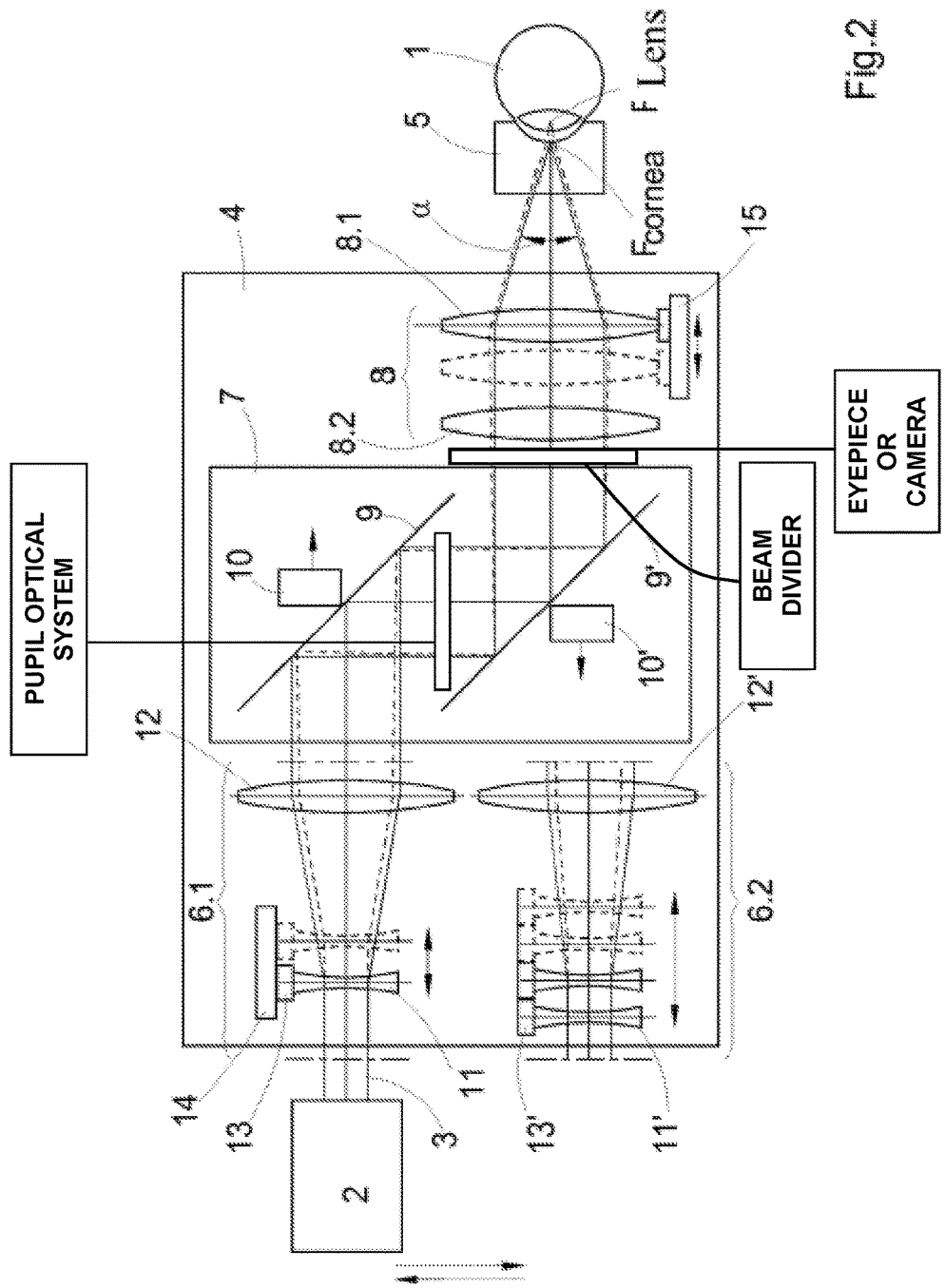
FIG. 2 is a schematic illustration of the invented optical system for a laser therapy instrument in a preferred embodiment.

FIG. 2 illustrates the operating principle of the optical system according to the invention. In this preferred embodiment, the objective 8 consists of two lens groups 8.1 and 8.2, which, for the sake of clarity, are represented symbolically as single lenses. The lens group 8.2 is arranged in a fixed position in the beam path, whereas the lens group 8.1 can be shifted in the direction of the optical axis and, for this purpose, is coupled with a straight-line guideway, which in turn is connected with, e.g., a linear drive motor 15, which initiates the shifting movement and is therefore triggered by a control device (not shown).

The distance by which the lens group 8.1 is shifted, while basically depending on the control signal, is favourably defined by two limit positions, of which a first limit position is marked in FIG. 2 by the lens group 8.1 drawn in solid lines and the second limit position by the same lens group drawn in broken lines.

The fixed shifting distance defined by the limit positions corresponds to the shifting of the focus position from the region of the cornea to the region of the crystalline lens and vice versa, by which it is made fundamentally possible that the laser therapy thus equipped can be used for treatments of both the cornea and the crystalline lens.

As the crystalline lens, as explained before, extends in axial direction over a substantially greater region than the cornea, different focus variation ranges $\Delta z$ are required for the two configurations, and measures must be taken to ensure that, despite the shifting of the focus from the region of the cornea to the region of the crystalline lens and the different focus variation ranges $\Delta z$ required for the two configurations, aberrations are as small as possible and the numerical aperture is a great as possible for the given wavelength of the therapeutic radiation.

According to example embodiments of the invention, this problem is solved by making separate optical assemblies 6.1, 6.2 available as expanders for each configuration and by exchanging these assemblies in the beam path for each other, for example automatically with the shifting of the focus position from the region of the cornea to the region of the crystalline lens and vice versa.

If, for example, the lens group 8.1 is in its first limit position and if at the same time—as shown in FIG. 2—the optical assembly 6.1 is in the beam path between the radiation source 2 and the deflecting device 7, the focus position can be changed—by means of the lens 11 in within a focus variation range $\Delta z1$ in Z-direction and by means of the deflecting device 7 in X- and Y-direction—in such a way that all desired targets within the region of the cornea can be reached with the desired optical precision.

Analogously, this also applies to the second limit position of the lens group 8.1. Simultaneously with the shifting of the lens group 8.1 its second limit position and, thus, the change of system configuration, the optical assembly 6.2 is positioned in the beam path between radiation source 2 and deflecting device 7 in place of the optical assembly 6.1, and thus, it is possible to reach all desired targets within the region of the crystalline lens, and this with the desired optical precision as well. The shifting of the lens 11' in Z-direction now causes the shifting of the focus position within a focus variation range $\Delta z2$, which corresponds to the extension of the region of the crystalline lens in the direction of the Z coordinate. The lateral variation of the focus position in X- and Y-direction within this region is accomplished by means of the deflecting device 7.

Since patient's eyes naturally differ in size and particularly in length, in a special embodiment of the invention the position/limit position of the lens group 8.1 for treating the crystalline lens is set as a function of the individual length of the eye, especially of the depth of the anterior chamber.

Both optical assemblies 6.1, 6.2 are so designed that the axially shiftable lenses or lens groups 11 or 11', respectively, in spite of the optical starting parameters brought about by the shifting have one and the same shifting distance, so that one and the same linear drive motor 14 with a specified, fixed shifting distance can be used for both configurations. However, the optical gear ratios of the two assemblies 6.1, 6.2 differ, so that, if the two assemblies 6.1, 6.2 are interchanged, the diameter of the therapeutic laser beam and, consequently, the numerical aperture and/or the eye-side aperture angle of the therapeutic laser radiation will change.

It is essential for the inventive idea that the optical assemblies 6.1, 6.2 consist of several lenses 11, 11', 12, 12' the axial distances between which can be varied. Due to the change of the axial distances, there will be a change of the refractive power situation within the optical assembly concerned, and thus a change of the axial focus position within the focus variation range $\Delta z1$ or $\Delta z2$, respectively. By contrast, the interchange of the optical assemblies 6.1, 6.2 causes a change of the diameter of the therapeutic laser beam and consequently, a change in the numerical aperture regarding the optical system behind the optical assemblies 6.1, 6.2 in the therapeutic laser beam path, and/or a change in the eye-side aperture angle of the therapeutic laser radiation.

Both optical assemblies 6.1, 6.2 have input and output interfaces in common with the other components of the optical system. The optical parameters at the input interface are always constant, whereas the output parameters vary depending on the optical assembly currently in the beam path and, thus, on the focus position to be set, and are characterized by different divergences and/or beam diameters.

In all embodiment versions of the invention, the changing device can be designed like a magazine, so that each of the two optical assemblies 6.1, 6.2 or also of further optical assemblies is assigned a mounting fixture, with which they, when required, are swivelled into the beam path about an axis of rotation or inserted by means of a straight-line guideway. The basic design of such magazines is known in prior art and needs no detailed description here.

The optical system may further include, between the optical assembly (6.1, 6.2) inserted in the therapeutic laser beam path and the objective a deflecting device for the lateral variation of the focus of the therapeutic laser radiation within the regions of the cornea and of the crystalline lens. This defecting device can for example be provided with two deflecting mirrors that are spaced apart and inclined relative to each other, and with a pupil optical system, for example imaging at a ratio of 1:1, being provided between the mirrors.

According to another example embodiment, in the beam path between the deflecting device and the objective, a beam divider is arranged for the purpose of coupling out a branch beam path directed at an eyepiece or a camera.

LIST OF REFERENCE NUMBERS 1 eye
2 radiation source
3 radiation beam
4 scanning device
5 contact glass
6 optical assembly
7 deflecting device
8 objective
8.1, 8.2 lens groups
9, 9' mirrors
10, 10' actuators
11, 11' lenses
12, 12' collective lenses
13, 13' straight-line guideway
14 linear drive motor
15 linear drive motor

What is claimed is:

1. An optical system for a laser therapy instrument, suitable for laser surgery of a cornea and/or a crystalline lens of an eye, comprising:
   a femtosecond laser radiation source that emits therapeutic laser radiation,
   an objective from which the therapeutic laser radiation exits and is directed and focussed on to or into the eye at a focus position, the objective itself or at least one lens or lens group of the objective being shiftable in the direction of the optical axis relative to other lenses or lens groups of the optical system, the shifting causing a shifting of a focus position from a region of the cornea to a region of the crystalline lens and vice versa,
   at least two optical assemblies that vary the focus of the therapeutic laser radiation, with a focus variation range $\Delta z$ of the at least two optical assemblies differing in size,
   a changing device that inserts one of the at least two optical assemblies at a time into a therapeutic laser beam path depending on the shifting of the focus position from the region of the cornea to the region of the crystalline lens and vice versa;
   a first optical assembly that covers a first focus variation range $\Delta z1$ extending over the axial extension of the cornea, and
   a second optical assembly that covers a focus variation range $\Delta z2$ extending over the axial extension of the crystalline lens.

2. The optical system as claimed in claim 1, wherein the shifting of the objective or the at least one lens or lens group of the objective in the direction of the optical axis relative to the other lenses or lens groups of the system is dependent on the individual eye length.

3. The optical system as claimed in claim 1, wherein the shifting of the objective or the at least one lens or lens group of the objective in the direction of the optical axis relative to the other lenses or lens groups of the system is dependent on a depth of the anterior chamber.

4. The optical system as claimed in claim 1, wherein
   the optical assemblies comprise several lenses the axial distances of which can be changed relative to each other, so that the refractive power ratio within the optical assemblies changes,
   the change of the refractive power ratio within the optical assembly currently in the therapeutic laser beam path causes an axial variation of the focus, and
   by interchanging the optical assemblies the diameter of the therapeutic laser beam is changed and, consequently, the numerical aperture with regard to the optical system behind the optical assemblies in the therapeutic laser beam path is changed, or the eye-side aperture angle of the therapeutic laser radiation is changed or a combination of the foregoing is changed.

5. The optical system as claimed in claim 4, in which the optical assemblies comprise at least one lens or lens group of negative refractive power, which are followed, in the direction of the beam, by a lens or lens group of positive refractive power, configured to change an internal refractive power ratio brought about by a change of axial distances between the at least one lens or lens group of negative refractive power and the lens or lens group of positive refractive power.

6. The optical system as claimed in claim 5, in which the at least two optical assemblies, to be interchangeable with other components of the optical system, comprise defined input and output interfaces, at which input parameters of the therapeutic laser beam path are constant, whereas the output parameters have different divergences, different beam diameters or both depending on the focus position to be set.

7. The optical system as claimed in claim 6, in which axially shiftable lenses or lens groups in all optical assemblies, in spite of the different output parameters achievable, are shifted through the same shifting distance and are coupled with a linear drive motor having a specified, fixed shifting distance, and optical gear ratio differs from assembly to assembly.

8. The optical system as claimed in claim 1, further comprising a changing device comprising a magazine structure with rotatable or straight-line shifting mounting fixtures for the optical assemblies.

9. The optical system as claimed in claim 1, further comprising, between one of the at least two optical assemblies when inserted in the therapeutic laser beam path and the objective, a deflecting device for lateral variation of the focus of the therapeutic laser radiation within the regions of the cornea and of the crystalline lens.

10. The optical system as claimed in claim 9, wherein the deflecting device comprises two deflecting mirrors that are spaced apart and that are inclinable relative to each other, and a pupil optical system between the two deflecting mirrors.

11. The optical system as claimed in claim 10, wherein the pupil optical system has an imaging ratio of 1:1.

12. The optical system as claimed in claim 9, further comprising a beam divider in the beam path between the deflecting device and the objective that couples out a branch beam path directed at an eyepiece or a camera.

13. The optical system as claimed in claim 1, further comprising a contact glass placed on the eye that suppresses eye movements.

14. The optical system as claimed in claim 1, in which
a first axial focus variation range $\Delta z$ in the region of the cornea is 0.5 mm to 2.0 mm, and
a second axial focus variation range $\Delta z$ in the region of the crystalline lens is 2 mm to 6 mm.

15. An optical system for a laser therapy instrument, suitable for laser surgery of a cornea and/or a crystalline lens of an eye, comprising:
a femtosecond laser radiation source that emits therapeutic laser radiation;
an objective from which the therapeutic laser radiation exits and is directed and focussed on to or into the eye at a focus position;
at least two optical assemblies that vary the focus of the therapeutic laser radiation, with a focus variation range $\Delta z$ of the at least two optical assemblies differing in size;
a changing device that inserts one of the at least two optical assemblies at a time into a therapeutic laser beam path;
a first optical assembly that covers a first focus variation range $\Delta z1$ extending over the axial extension of the cornea; and
a second optical assembly that covers a focus variation range $\Delta z2$ extending over the axial extension of the crystalline lens.

* * * * *